United States Patent [19]

Cadossi et al.

[11] Patent Number: 4,683,873
[45] Date of Patent: Aug. 4, 1987

[54] METHOD AND DEVICE FOR TREATING LIVING TISSUES AND/OR CELLS BY MEANS OF PULSATING ELECTROMAGNETIC FIELDS

[76] Inventors: Ruggero Cadossi; Donata Marazzi, both of Via Geminiola, 1, 42015 Correggio (Reggio Emilia), Italy

[21] Appl. No.: 928,935

[22] Filed: Nov. 12, 1986

Related U.S. Application Data

[63] Continuation of Ser. No. 616,318, Jun. 1, 1984, abandoned.

[30] Foreign Application Priority Data

Jun. 2, 1983 [IT] Italy ................................ 67613 A/83

[51] Int. Cl.4 ................................................ A61N 1/40
[52] U.S. Cl. .................................. 128/1.5; 128/419 F
[58] Field of Search .............. 128/1.5, 419 F, 421–427

[56] References Cited

U.S. PATENT DOCUMENTS

| | | | |
|---|---|---|---|
| 3,893,462 | 7/1975 | Manning | 128/421 |
| 4,105,017 | 8/1978 | Ryaby et al. | 128/419 F X |
| 4,266,532 | 5/1981 | Ryaby et al. | 128/419 F X |
| 4,428,366 | 1/1984 | Findl et al. | 128/1.5 |

OTHER PUBLICATIONS

Bassett et al., "Augmentation of Bone Repair . . . ", Science, vol. 184, pp. 575–577, May 1974.
Cadossi, R. et al., "Low Frequency Pulsing Electromagnetic Fields in the Treatment of Delayed Unions and Acquired Pseudo-Arthrosis", Abstract, 2nd Annual BRAGS, Oxford, U.K. Sep. 20–22, 1982.
Bassett, C. A. L. et al.; "A Non-Operative Salvage of Surgically-Resistant Pseudarthroses and Non-Unions by Pulsing Electromagnetic Fields: A Preliminary Report"; *Clin. Orthoped. and Rel. Research;* No. 124; pp. 128 to 143, (May 1977).

*Primary Examiner*—Lee S. Cohen
*Attorney, Agent, or Firm*—Charles J. Knuth; Peter C. Richardson; Lawrence C. Akers

[57] ABSTRACT

A method for treating living tissues and/or cells consisting essentially of electromagnetically inducing in the tissue and/or cells alternating pulsating electrical signals having a wave form which comprises a positive portion with a duration of between 1 and 3 milliseconds, and a negative portion having a peak value less than that of the positive portion, followed by a region of exponential extension tending to the reference value zero.

13 Claims, 3 Drawing Figures

King
METHOD AND DEVICE FOR TREATING LIVING TISSUES AND/OR CELLS BY MEANS OF PULSATING ELECTROMAGNETIC FIELDS This is a continuation of application Ser. No. 616,318, filed on June 1, 1984, now abandoned.

BACKGROUND OF THE INVENTION

This invention relates to a method and a device for treating living tissues and/or cells by means of pulsating electromagnetic fields.

It is known to use pulsating electromagnetic fields for inducing alternating electrical signals in the tissue or cells, such signals having proved particularly effective in promoting healing both in the case of delayed union fractures and pseudarthroses and in the case of associated cutaneous lesions of traumatic or vascular origin. In this respect, delayed union fractures are considered to be those bone fractures characterized by low presence of bone callus and lack of rearrangement of the fragments at least six months after the trauma, whereas it is more proper to speak of pseudarthroses when a clear morbid state with pathological evolution of the callus formation process is present at least ten months after the trauma. Currently known apparatus able to effect the aforesaid treatment can be essentially divided into two types. In the first type of apparatus, low impedance solenoids are used for generating the magnetic field. Such solenoids enable intense electric currents to be induced in the tissues, but only for very short times (less than 300 microseconds), because of which it is necessary to use so-called "pulse trains" in order to obtain a sufficient effect on the tissue. The second known type of apparatus comprises an iron core inside the solenoids, this enabling a magnetic field of considerable intensity to be used, and correspondingly allowing less intense currents to be induced, but for considerably longer times. Neither of the aforesaid apparatus has ever promoted the union of a pseudarthrosis by the formation of periosteal callus, and moreover they cannot be applied in the case of so-called "fresh" fractures, i.e. fractures which have just occurred.

SUMMARY OF THE INVENTION

The object of the present invention is to define a method and a device for treating living tissues and/or cells by means of pulsating electromagnetic fields which, especially with regard to treatment of fractures (delayed union fractures and pseudarthroses), enables better results to be obtained than devices of known type, and in particular favors the formation of periosteal callus for joining the opposing ends of the fracture.

Said object is attained according to the present invention by a method for treating living tissues and/or cells by means of pulsating electromagnetic fields, characterized by electromagnetically inducing, in the tissue and/or cells, alternating pulsating electrical signals having a wave form which comprises a positive portion composed, in chronological order, of a first, a second and a third segment, the first of which defines the peak value of said positive portion, and a negative portion composed respectively of a segment which defines the peak value and constitutes the prolongation of the third segment of said positive portion, and of a region of exponential extension tending to the reference value zero; the duration of said positive portion being between 1 and 3 milliseconds.

The present invention also relates to a device for treating living tissues and/or cells by means of pulsating electromagnetic fields, characterized by at least one inductor and at least one square-wave signal generator circuit feeding said inductor in such a manner that this latter generates an alternating pulsating electromagnetic field which, within said tissue and/or cells, induces electrical signals having a wave form which comprises a positive portion composed, in chronological order, of a first, a second and a third segment, the first of which defines the peak value of said positive portion, and a negative portion composed respectively of a segment which defines the peak value and constitutes the prolongation of the third segment of said positive portion, and of a region of exponential extension tending to the reference value zero; the duration of said positive portion being between 1 and 3 milliseconds.

These and other objects, features and advantages of the invention will become evident in light of the following detailed description, viewed in conjunction with the referenced drawings, of a preferred Method and Device for Treating Living Tissues and/or Cells by Means of Pulsating Electromagnetic Fields according to the invention. The foregoing and following description of the invention is for exemplary purposes only. The true spirit and scope of the invention is set forth in the appended claims.

DETAILED DESCRIPTION

Figure 1:
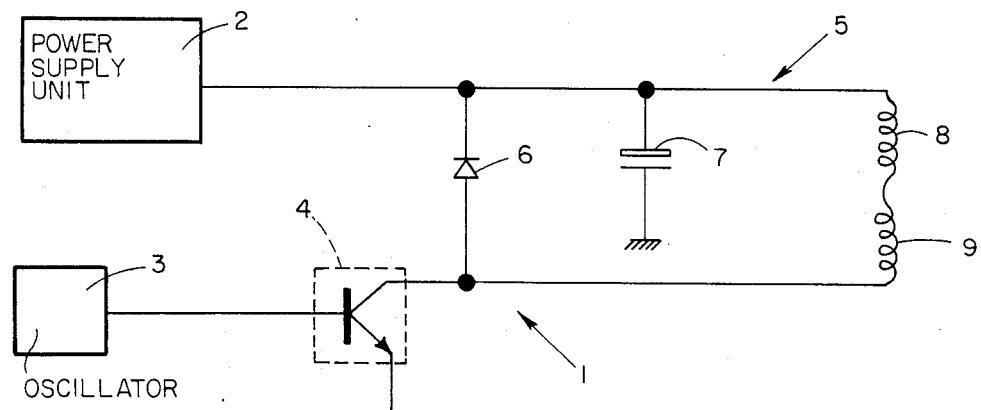
FIG. 1 shows a simplified block diagram of a device constructed in accordance with the present invention.

In FIG. 1, the reference numeral 1 indicates generally a device able to generate a pulsating electromagnetic field in accordance with the requirements of the present invention. The device 1 comprises essentially a power supply unit 2 able to provide an adjustable D.C. voltage, an oscillator 3 able to generate a square wave, a power stage 4 connected to the output of the oscillator 3, and an oscillation circuit 5 connected between the outputs of the stage 4 and power supply unit 2. Specifically, the output of the power supply unit 2, at which a voltage conveniently adjustable between 100 and 300 volts is present, is connected respectively to the cathode of a diode 6, to the first terminal of a capacitor 7 having its second terminal connected to earth, and to the first terminal of an inductor 8, which is connected in series with a further inductor 9, both being connected in parallel with the diode 6. Conveniently, the inductors 8 and 9 each have a number of turns exceeding 1000 and an impedance which, according to the type of winding, can vary between 400 and 600 ohms. The frequency of the oscillator 3 is suitably chosen at a value greater than 50 Hz, such as to control the positioning of the anode of the diode 6, by way of the power stage 4, alternately at the voltage value present at the output of the power supply unit 2 and at earth.

Figure 2:
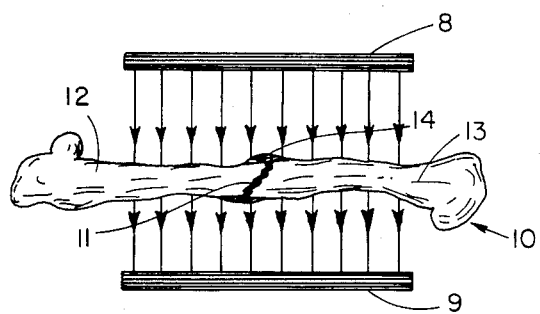
FIG. 2 is a diagrammatic view of an applicational example of the device of FIG. 1.

In FIG. 2, the reference numerals 8 and 9 indicate the inductors of FIG. 1, between which there is positioned a limb 10 (of which only the bone structure is shown) comprising a fracture in a zone indicated by 11. The constituent bone of the limb 10 is thus divided into two portions 12 and 13 disposed facing each other at the zone 11, about which a periosteal callus is indicated by 14.

Figure 3:
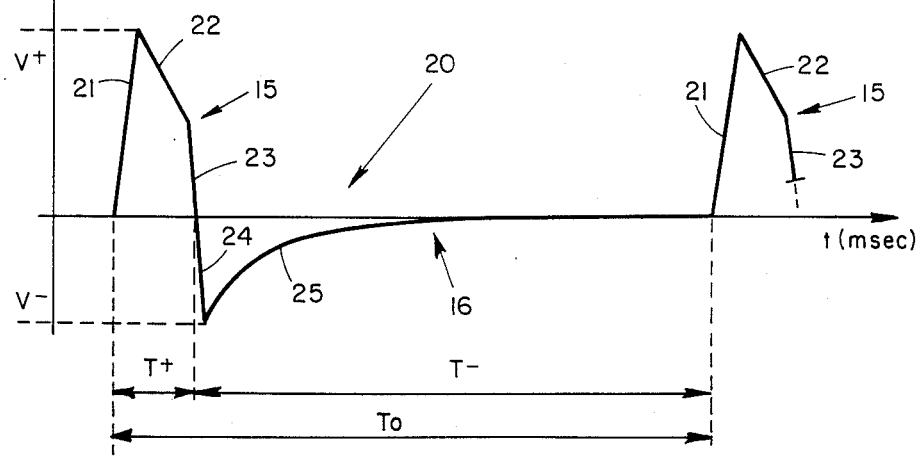
FIG. 3 shows a wave form obtained by the device of FIG. 1 and determined by means of a suitable sensor.

FIG. 3 shows the pattern of the electrical signal (20 in FIG. 3) determined by means of a suitable probe (not shown) disposed in the zone 11 of FIG. 2. Said electrical signal 20 is of the alternating periodical type, with a repetition period, indicated by $T_0$, which depends on the frequency at which the signal of the oscillator 3 is emitted. The signal 20 has a positive portion 15 and a negative portion 16, of which the time durations are indicated respectively by $T+$ and $T-$. Specifically, the positive portion 15 is essentially composed, in chronological order, of three segments indicated respectively by 21, 22, and 23, the first (21) of which defines the peak value ($V+$) of said positive portion 15. The negative portion is essentially composed of a segment 24 which constitutes the prolongation of the segment 23 and defines the peak value, indicated by $V-$, of the negative portion 16. This latter also comprises a region 25 of exponential extension tending to the reference value zero. Conveniently, the values between which the peak voltage V varies lie essentially between 1.2 and 5 millivolts. The length of the segment 21 is approximately double that of the segment 23, which in its turn is almost equal to the segment 24. As shown in FIG. 3 the positive portion 15 of the signal 20, taken together with the zero voltage base line, has substantially the shape of a trapezium.

With regard to the times, the duration of the half period $T+$ is conveniently between 1 and 3 milliseconds, and this range of values is to be considered essential for the purposes of the therapeutic results obtained by the method of the present invention.

With regard to operation, certain precautions must be taken before using the device 1 for therapeutic treatment. In particular, the zone surrounding the fracture must be immobilized. This immobilization can be entrusted to internal or external synthesis means, provided they do not possess magnetic properties which would interfere with the induced field, or to plaster casts. Such immobilization should be rigorous because the persistence of micromovements can be a cause of failure of the therapy. Even with tightened pseudarthroses it is often convenient to use a light plaster case, a leather appliance or a brace.

The axiality of pseudarthrosis ends must be excellent. Rough angular or rotary deformities should be previously corrected where possible.

Having taken these precautions, the inductors 8 and 9 are disposed as shown in FIG. 2, i.e. such that the zone 11 to be treated is as far as possible in the center of the zone bounded by the solenoids. The voltage generated by the power supply unit 2 is adjusted as required, taking account of the distance between the inductors 8 and 9, in order to induce in the bone tissue a current density of between 2 and 30 microamperes/cm². At this point the stimulation is started, and the electrical signal induced in the zone 11 to be treated is essentially that shown in FIG. 3, with a positive half period of duration $T+$ which, as stated, is essentially between 1 and 3 milliseconds. The minimum daily duration of stimulation must be between 8 and 14 hours, not necessarily continuous. It is also possible to carry out treatment during night hours. In order to center the zone 11 between the inductors 8 and 9 the greatest possible accuracy, it is advisable to carry out a radiographic check along two mutually perpendicular projections, in order to ensure that the magnetic field lines of force, indicated in FIG. 2, are exactly perpendicular to the major axis of the skeletal segment treated.

It has been found that the signal 20 illustrated in FIG. 3 promotes healing through an intense stimulation towards the formation of periosteal callus, this being interpreted as a consequence of the strong vascular effect which is induced precisely by virtue of the considerably greater duration of the half period $T+$ than analogous half periods of induced signals in the case of the aforesaid devices of known type.

Finally, it is apparent that modifications can be made to the described method and device without leaving the present invention. In particular, as it has been reliably demonstrated that pulsating electromagnetic fields have a favorable effect on tissue repair processes at all levels (osteocartilaginous, nervous, vascular, paranchymal etc.), it is apparent that the described method can also be advantageously applied in treatments which are outside the pathology described by way of example. In this respect, it has been recently observed that the aforesaid method and device also enable significant results to be obtained in the field of so-called "fresh" fractures.

Although the invention has been described in conjunction with the foregoing specific embodiment many alternatives, variations and modifications are apparent to those of ordinary skill in the art. Those alternatives, variations and modifications are intended to fall within the spirit and scope of the appended claims.

We claim:

1. A method for treating living bone tissue by means of pulsating electromagnetic fields to stimulate the growth of said tissue, consisting essentially of electromagnetically inducing in the tissue alternating pulsating electrical signals having a wave form which comprises a positive portion composed, in chronological order, of a first, a second and a third segment, the first of which defines the peak value of said positive portion, and a negative portion composed respectively of a segment which defines the peak value and constitutes the prolongation of the third segment of said positive portion and a region of exponential extension tending to the reference value zero; the positive portion taken together with the zero signal base line having substantially the shape of a trapezium, the peak value of the positive portion being greater in absolute magnitude than the peak value of the negative portion, the duration of said positive portion being between 1 and 3 milliseconds and the frequency of repetition of said pulsating electrical signals being greater than 50 Hz, with said treatment causing substantial formation of periosteal callus in the region of said bone tissue growth.

2. A method as claimed in claim 1, wherein said electromagnetic field has a value such as to induce in said tissue a current density of between 2 and 30 microamperes/cm².

3. A method as claimed in claim 2 wherein the duration of the treatment is between 8 and 14 hours per day.

4. A method as claimed in claim 2 wherein in that the zone subjected to treatment is immobilized by suitable means not possessing magnetic properties.

5. A method as claimed in claim 1 wherein the duration of the treatment is between 8 and 14 hours per day.

6. A method as claimed in claim 5 wherein the zone subjected to treatment is immobilized by suitable means not possessing magnetic properties.

7. A method as claimed in claim 1 wherein the zone subjected to treatment is immobilized by suitable means not possessing magnetic properties.

8. A device for treating living bone tissue by means of pulsating electromagnetic fields to stimulate the growth of said tissue, comprising a D.C. power supply unit having an output, oscillator means capable of generating a square wave and having an output, and an oscillation circuit connected across the outputs of said power supply unit and oscillator means, said oscillator circuit including at least one inductor which generates an alternating pulsating electromagnetic field which, within said tissue, induces electrical signals having a wave form which comprises a positive portion composed, in chronological order, of a first, a second and a third segment, the first of which defines the peak value of said positive portion, and a negative portion composed respectively of a segment which defines the peak value and constitutes the prolongation of the third segment of said positive portion, and a region of exponential extension tending to the reference value zero; the positive portion taken together with the zero signal base line having substantially the shape of a trapezium, the peak value of the positive portion being greater in absolute magnitude than the peak value of the negative portion, the duration of said positive portion being between 1 and 3 milliseconds and the oscillation frequency of said oscillator means being greater than 50 Hz, whereby said treatment causes substantial formation of periosteal callus in the region of said bone tissue growth.

9. A device as claimed in claim 8 wherein said oscillation circuit further includes a diode connected between the outputs of said power supply unit and oscillator means, and a capacitor connected between the output of said power supply unit and ground, with said diode and said at least one inductor being connected in parallel.

10. A device as claimed in claim 9 wherein said device further comprises means for adjusting the voltage generated by said power supply unit between 100 and 300 volts.

11. A device as claimed in claim 10, wherein said inductor has an impedance of between 400 and 600 ohms.

12. A device as claimed in claim 9, wherein said inductor has an impedance of between 400 and 600 ohms.

13. A device as claimed in claim 12, wherein said oscillation circuit includes a pair of inductors, between which, when in operation, there is placed said tissue to be subjected to treatment.

* * * * *